US00PP08125P

United States Patent [19]

Fruehwirth

[11] Patent Number: Plant 8,125

[45] Date of Patent: Feb. 2, 1993

[54] POINSETTIA PLANT NAMED 268 WHITE

[75] Inventor: Franz Fruehwirth, Encinitas, Calif.

[73] Assignee: Paul Ecke Ranch, Inc., Encinitas, Calif.

[21] Appl. No.: 730,350

[22] Filed: Jul. 15, 1991

[51] Int. Cl.[5] ..... A01H 5/00

[52] U.S. Cl. ..... Plt./86.2

[58] Field of Search ..... Plt./86.1-86.4

[56] References Cited

U.S. PATENT DOCUMENTS

P.P. 7,275 7/1990 Fruehwirth ..... Plt. 86.4

*Primary Examiner*—James R. Feyrer

*Attorney, Agent, or Firm*—Arnold, White & Durkee

[57] ABSTRACT

This new Poinsettia cultivar, designated '268 White', is a vigorous plant with erect, large white bracts. Cultivar '268 White' is a sport of the red bracted cultivar '268' (U.S. Plant Pat. No. 7,275), and, like its parent, is unique because the flower bracts remain erect and do not droop, even after commercial shipping and handling or as the flowers mature. It always looks "fresh" which adds to its beauty and increases its value as a consumer product. Poinsettia '268 White' has the same flowering response time and cultural requirements as its parent '268'.

1 Drawing Sheet

BACKGROUND OF THE INVENTION

This new Poinsettia cultivar originated as a color sport of '268' (U.S. Plant Pat. No. 7,275) in a greenhouse in Encinitas, Calif. It was selected from many plants because of its large, erect and white flower bracts and self-branching traits, which distinguish it from other poinsettia cultivars and makes it a desirable plant for commercial greenhouse production. After selection, vegetative reproduction of this plant has accomplished by stem cuttings for test purposes in Encinitas, Calif., and clones of the plant were subjected to successive generations of vegetative propagation, which demonstrated that its distinct characteristics hold true from generation to generation.

DESCRIPTION OF THE PHOTOGRAPHS

Poinsettia '268 White' is illustrated in the accompanying color photographs.

The upper photo is a side view of one pinched '268 White' plant in a 14 cm. pot.

The lower photo is a top view of an unpinched '268 White' plant showing flower and bract formation.

DESCRIPTION OF THE PLANT

The following is a detailed description of this new Poinsettia as observed in my greenhouse in Encinitas, Calif., during December, 1990. Recorded observations from flowering plants, grown as 3 unpinched plants per pot, were observed. The pot was 14 cm. in diameter and 11 cm. in height. Color designations were compared to the 1986 edition of R.H.S. Colour Chart, first published in 1966 by the Royal Horticultural Society, London, England.

THE PLANT

Origin: Sport of '268' (U.S. Plant Pat. No. 7,275).

Classification:

*Botanic.*—*Euphorbia pulcherrima* Willd.

*Common name.*—Poinsettia.

*Cultivar name.*—'268 White'.

Form: Shrub.

Height: Short to medium.

Growth habit: As a single stemmed plant, upright and vigorous with many self-branching axillary stems. The application of a chemical growth retardant may not be needed to restrict height for commercial pot plant production. Observations of 3 plants in a pot with an overall height of 46 cm. and an overall width of 49 cm. were made. The bract diameter of individual flowers was 28 cm.

Branching: Poinsettia '268 White', like its parent plant '268', has self-branching traits. Branching can be enhanced by removal of the stem tip. Then, several flowering branches with equal vigor will develop on a single plant.

Growth rate: Very fast. Rooting of stem cuttings occurs in 12-18 days under intermittent mist. The plant will flower in about nine weeks under continuous long night conditions and night temperatures of about 16-18 degrees C.

Foliage: The foliage is clean and uniformly green from bottom to top of the plant. The leaves are of medium size, leaf blades typically being 12-13 cm. long and 9-10 cm. wide with leaf petioles 5-6 cm. long.

*Leaf shape.*—Typical leaves are ovate with acute bases and acuminate tips. Leaf margins are slightly lobed with 1 or 2 indentations on each side of the leaf blade.

*Color.*—Upper side — Green, darker than RHS 147A. Under side — Green, near RHS 147B.

*Retention.*—The foliage lasts fairly well even under low light intensities in the consumer's home.

Bracts: Generally there are 18-24 uniformly colored bracts of various sizes subtending the cyathia. The primary bracts have blades typically 14-15 cm. long and 10-12 cm. wide with petioles 3-4 cm. long. Bract attitude is erect for both '268 White' and its parent '268'.

*Shape.*—Bracts are mostly ovate, but elliptic for the smaller bracts, with acute bases and acuminate tips. Primary bracts are lobed with two indentations on either side of the bract. Secondary bracts have entire margins.

*Color.*—Upper side — Creamy white, darker than RHS 155A, near RHS 4D. Under side —

Creamy white, darker than RHS 155A, near RHS 4D.

Flowers: Generally, 18–24 cyathia (flowers) are present when the plant is in full bloom. Each cyathium is 6–7 mm long and 5 mm wide, green in color, and fringed with yellow at the distal end. One yellow nectar cup protrudes from the side of each cyathium. The flower pedicel is also green and about 4–5 mm in length. The stamens protruding from the cyathia are white.

What is claimed is:

1. A new and distinct Poinsettia cultivar, substantially as herein shown and described, characterized by its large white, erect flower bracts, and self-branching traits.

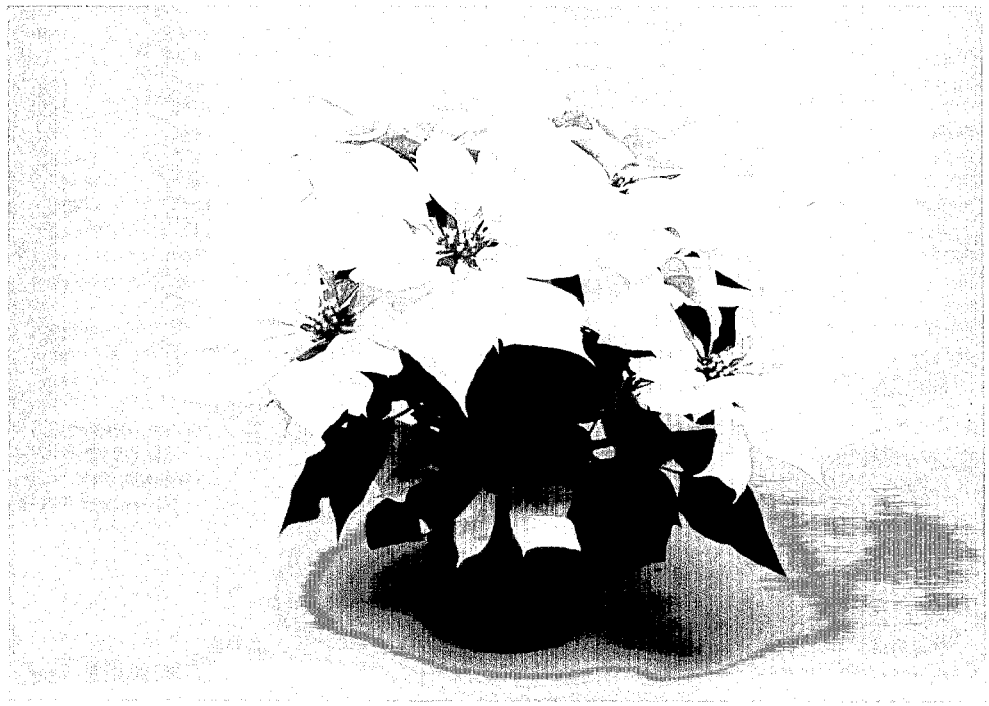
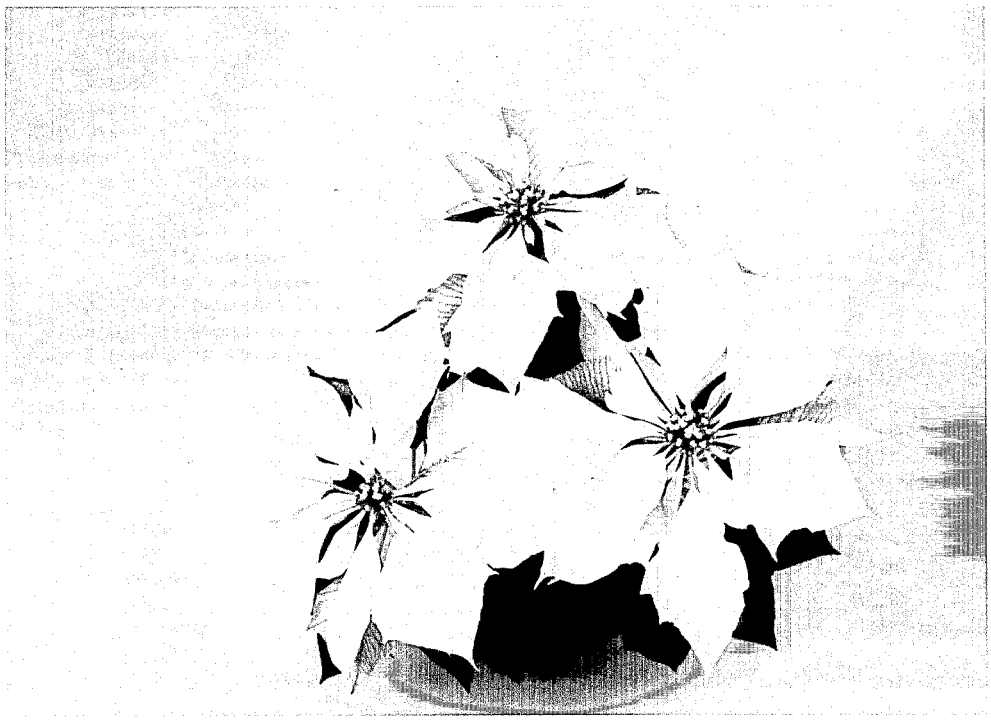

* * * * *